United States Patent
Kudoh

(10) Patent No.: US 11,106,147 B2
(45) Date of Patent: Aug. 31, 2021

(54) ELECTROPHOTOGRAPHIC PHOTOCONDUCTOR

(71) Applicant: Konica Minolta, Inc., Tokyo (JP)

(72) Inventor: Koichi Kudoh, Hino (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 16/896,833

(22) Filed: Jun. 9, 2020

(65) Prior Publication Data

US 2021/0011391 A1    Jan. 14, 2021

(30) Foreign Application Priority Data

Jul. 12, 2019   (JP) .............................. JP2019-130275

(51) Int. Cl.
   *G03G 5/14*   (2006.01)
   *G03G 5/06*   (2006.01)
   (Continued)

(52) U.S. Cl.
   CPC ......... *G03G 5/0655* (2013.01); *C07D 471/16* (2013.01); *G03G 5/047* (2013.01);
   (Continued)

(58) Field of Classification Search
   CPC ............. G03G 5/0614; G03G 5/06142; G03G 5/06144; G03G 5/061443; G03G 5/061446
   See application file for complete search history.

(56) References Cited

U.S. PATENT DOCUMENTS

| | | | | |
|---|---|---|---|---|
| 2009/0162768 A1* | 6/2009 | Wu | ...................... | G03G 5/0514 430/58.35 |
| 2011/0143273 A1* | 6/2011 | Sekido | ................. | G03G 5/0535 430/56 |
| 2015/0192869 A1* | 7/2015 | Takezawa | .......... | G03G 5/14795 430/56 |

FOREIGN PATENT DOCUMENTS

JP       2007-199400 A    8/2007

* cited by examiner

*Primary Examiner* — Peter L Vajda
(74) *Attorney, Agent, or Firm* — Lucas & Mercanti, LLP

(57) ABSTRACT

There is provided an electrophotographic photoconductor in which at least an undercoat layer and a photosensitive layer are laminated in an order mentioned on a conductive support,
   wherein at least one of the undercoat layer and the photosensitive layer contains a compound represented by a formula A below:

[Chemical 1]

(FORMULA A)

wherein Y in the above formula A is a group represented by:

[Chemical 2]

wherein R1 and R2 are each independently an alkyl group having 1 to 6 carbon atoms, m is an integer of 1 to 4, and X is each independently a group selected from a group 1 below:

(Continued)

[Chemical 3]
(GROUP 1)
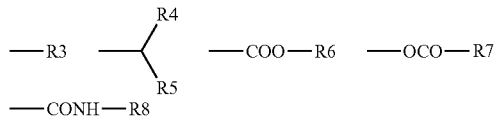
wherein R3 to R8 in the above group 1 are each independently an alkyl group having 1 to 6 carbon atoms.
9 Claims, 2 Drawing Sheets
(51) Int. Cl.
    *G03G 5/047*     (2006.01)
    *C07D 471/16*     (2006.01)
(52) U.S. Cl.
    CPC ....... *G03G 5/0696* (2013.01); *G03G 5/06142* (2020.05); *G03G 5/06144* (2020.05); *G03G 5/144* (2013.01)

ELECTROPHOTOGRAPHIC PHOTOCONDUCTOR

The entire disclosure of Japanese patent Application No. 2019-130275, filed on Jul. 12, 2019, is incorporated herein by reference in its entirety.

BACKGROUND

Technological Field

The present invention relates to an electrophotographic photoconductor.

Description of the Related Art

An electrophotographic image forming apparatus employs an electrophotographic photoconductor (hereinafter also simply referred to as a "photoconductor") in order to form an electrostatic latent image corresponding to an image to be formed. The electrostatic latent image is formed by irradiating the surface of a charged photoconductor with light. When toner is supplied to the photoconductor on which the electrostatic latent image is formed, a toner image is formed. The toner image is transferred to a recording medium.

Some known photoconductors have a configuration in which an undercoat layer and a photosensitive layer are laminated in the order mentioned on a conductive support. Some known photosensitive layers have a configuration in which, for example, a charge generation layer and a charge transport layer are laminated in the order mentioned.

Image is formed by rotating the photoconductor so as to be repeatedly subjected to an image formation process (a charging step, an image exposure step, a development step, a transfer step, a cleaning step, and a neutralization step). During the process, an image formation history of the previous rotation may not be sufficiently erased, and resultingly image memory (ghost) accompanied by the history may occur in the image formation process of the following rotation. Image memory includes negative memory and positive memory (FIGS. 1A to 1C). The negative memory is a phenomenon in which, for example, after a black solid image is printed in the previous rotation, the halftone portion corresponding to the black solid portion in the previous rotation is printed in lighter tone in the following rotation (FIG. 1B). The positive memory is a phenomenon in which, for example, after a black solid image is printed in the previous rotation, the halftone portion corresponding to the black solid portion in the previous rotation is printed in darker tone in the following rotation (FIG. 1C).

So far, various studies have been conducted in order to suppress the occurrence of image memory. For example, JP 2007-199400 A states that the occurrence of image memory is suppressed by containing a naphthalenetetracarboxylic acid diimide compound in the photosensitive layer.

However, the photoconductor employing the compound described in JP 2007-199400 A is not exactly capable of suppressing the occurrence of image memory (ghost) to a sufficient degree. Furthermore, the photoconductor employing the compound described in JP 2007-199400 A does not show satisfactory potential stability during long-term repeated use.

SUMMARY

Therefore, an object of the present invention is to provide an electrophotographic photoconductor that is capable of suppressing the occurrence of image memory (ghost) and exhibits excellent potential stability during long-term repeated use.

To achieve the abovementioned object, according to an aspect of the present invention, there is provided an electrophotographic photoconductor, reflecting one aspect of the present invention, in which at least an undercoat layer and a photosensitive layer are laminated in an order mentioned on a conductive support, wherein at least one of the undercoat layer and the photosensitive layer contains a compound represented by a formula A below:

[Chemical 1]

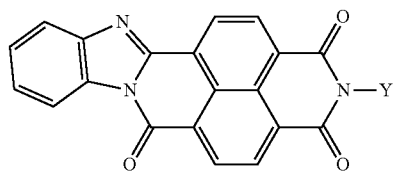

(FORMULA A)

wherein Y in the above formula A is a group represented by:

[Chemical 2]

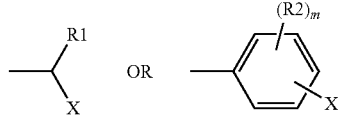

wherein R1 and R2 are each independently an alkyl group having 1 to 6 carbon atoms, m is an integer of 1 to 4, and X is each independently a group selected from a group 1 below:

[Chemical 3]

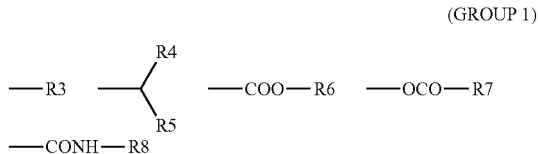

(GROUP 1)

wherein R3 to R8 in the above group 1 are each independently an alkyl group having 1 to 6 carbon atoms.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1A:
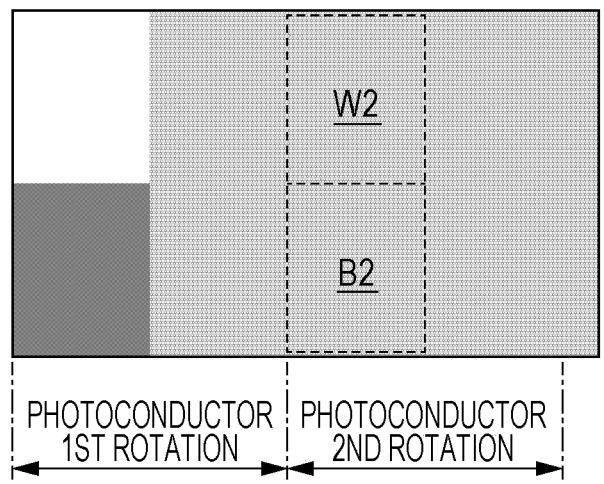
FIGS. 1A to 1C are schematic diagrams for explaining image memory (negative memory and positive memory)

Hereinafter, one or more embodiments of the present invention will be described with reference to the drawings. However, the scope of the invention is not limited to the disclosed embodiments. Note that the phrase "x to y" as used herein expressing a range includes both x and y and means "equal to or greater than x and equal to or less than y". In addition, unless otherwise specified herein, operation and measurement of physical properties and the like are performed under the conditions of room temperature (20 to 25° C.)/relative humidity of 40 to 50% RH.

Note that "(meth)acryl" herein refers to "acryl and/or methacryl".

An electrophotographic photoconductor according to an embodiment of the present invention is an electrophotographic photoconductor in which at least an undercoat layer and a photosensitive layer are laminated in the order mentioned on a conductive support, and at least one of the undercoat layer and the photosensitive layer contains a compound represented by the formula A below:

[Chemical 4]

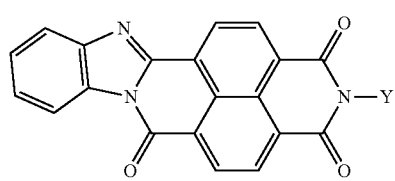

(FORMULA A)

in the formula A above, Y is a group represented by:

[Chemical 5]

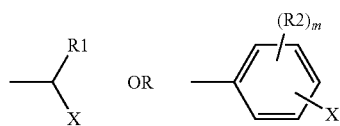

where R1 and R2 are each independently an alkyl group having 1 to 6 carbon atoms, m is an integer of 1 to 4, and X is each independently a group selected from the group 1 below:

[Chemical 6]

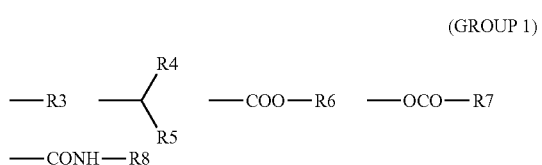

(GROUP 1)

in the group 1 above, R3 to R8 are each independently an alkyl group having 1 to 6 carbon atoms.

The electrophotographic photoconductor is capable of suppressing the occurrence of image memory (ghost) and exhibits excellent potential stability during long-term repeated use. Details of the reason why such effect is provided are unknown, but are considered to be owing to the following mechanism.

A generally known electrophotographic photoconductor has a configuration in which an undercoat layer and a photosensitive layer are laminated in the order mentioned on a conductive support. The undercoat layer has a function of transporting electrons generated in the photosensitive layer to the conductive support (electron transport property) and a function of preventing injection of holes from the conductive support into the photosensitive layer (hole blocking property). However, image memory will occur if these functions are insufficiently fulfilled. The reason therefor is not clear, but is presumed as follows. For example, when the undercoat layer has an insufficient electron transporting property, electrons generated through exposure remain in the undercoat layer, and resultingly holes generated through the exposure are trapped in the photosensitive layer, and the holes are not fully transported to the surface of the photoconductor. A conceivable result is that negative charges in the exposure unit are not canceled out, and the toner failing to adhere to the exposure unit is transferred to the recording medium, whereby negative memory occurs. When the undercoat layer has an insufficient hole blocking property, holes injected from the conductive support more easily migrate to the surface of the photoconductor. A conceivable result is that the surface potential of the exposure unit changes to the positive side, and the toner excessively adhering to the exposure unit is transferred to the recording medium, whereby positive memory occurs.

On the basis of the above presumption, it is considered that adding an electron transport material to the undercoat layer improves the electron transport property and hole blocking property of the undercoat layer to suppress the occurrence of image memory. However, studies conducted by the present inventor found that the photoconductor produced by adding the electron transport material described in JP 2007-199400 A to the undercoat layer could not sufficiently suppress the occurrence of image memory (negative memory). In addition, the photoconductor underwent significant variations in exposure potential during long-term repeated use to reveal that the photoconductor did not have satisfactory potential stability (Comparative Example 3 described later).

Therefore, the present inventor has conducted intensive studies on the design of the electron transport material. As a result, it has been found that using a compound in which a benzimidazole ring is introduced on one side of a naphthalenetetracarboxylic acid diimide skeleton as represented by the above formula A can provide a photoconductor that exhibits excellent potential stability during long-term repeated use while suppressing the occurrence of image memory (ghost). It is considered that incorporating the compound represented by the formula A into the undercoat layer improved the electron transport property and the hole blocking property of the undercoat layer, and resultingly image memory was suppressed. In addition, it is considered that incorporating the compound represented by the formula A into the undercoat layer or the photosensitive layer improved the charge retention property and photosensitivity of the photoconductor, and resultingly the potential stability during long-term repeated use was improved.

Note that the mechanism described above is based on a presumption and its correctness does not affect the technical scope of the present embodiment.

The following describes a configuration of an electrophotographic photoconductor according to the present invention.

<Conductive Support>

A conductive support included in the photoconductor of the present invention is a member that supports an undercoat layer and a photosensitive layer and has electric conductivity.

Examples of the conductive support include a metal drum or sheet, a plastic film having a laminated metal foil, a plastic film having a layer of a deposited conductive material, and a metal member, a plastic film, or paper having a conductive material or a conductive layer formed by applying a coating that includes a conductive material and a binder resin. Examples of the aforementioned metal include aluminum, copper, chromium, nickel, zinc, and stainless steel. From the viewpoint of workability, robustness, and lightness, the aforementioned metal is preferably aluminum. Examples of the aforementioned conductive material include the aforementioned metals, indium oxide, and tin oxide.

<Undercoatlayer>

An undercoat layer included in the photoconductor of the present invention has a function of transporting charges (such as electrons) generated in the photosensitive layer to the conductive support and a function of preventing injection of charges (such as holes) from the conductive support to the photosensitive layer. In addition, the undercoat layer has a function of adhering the conductive support and the photosensitive layer to each other.

[Compound Represented by Formula A]

In the present invention, the undercoat layer preferably contains a compound represented by the formula A (hereinafter also referred to as a "compound A"). The compound A may be of a single type or of two or more types.

[Chemical 7]

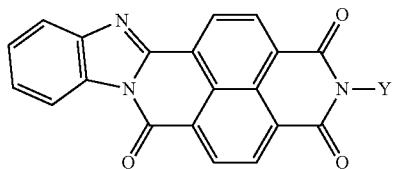

(FORMULA A)

in the formula A above, Y is a group represented by:

[Chemical 8]

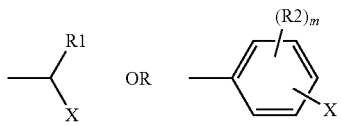

where R1 and R2 are each independently an alkyl group having 1 to 6 carbon atoms, m is an integer of 1 to 4, and X is each independently a group selected from the following group 1:

[Chemical 9]

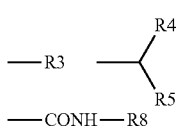

(GROUP 1)

in the group 1 above, R3 to R8 are each independently an alkyl group having 1 to 6 carbon atoms.

From the viewpoint of further improving effects of the present invention, m is preferably an integer of 1 to 3, more preferably 1 or 2, and still more preferably 2.

The alkyl group having 1 to 6 carbon atoms may be linear or branched, and examples of the alkyl group include a methyl group, an ethyl group, a propyl group, an isopropyl group, an n-butyl group, a sec-butyl group, a tert-butyl group, an n-pentyl group, an isopentyl group, a sec-pentyl group, a tert-pentyl group, a neopentyl group, an n-hexyl group, an isohexyl group, and a cyclohexyl group.

From the viewpoint of further improving effects of the present invention, R1 and R2 are each independently preferably a methyl group or an ethyl group, and more preferably a methyl group.

From the viewpoint of further improving effects of the present invention, in the aforementioned group 1, R3 to R5 are each independently preferably a methyl group or an ethyl group, and more preferably a methyl group.

From the viewpoint of further improving effects of the present invention, in the aforementioned group 1, R6 to R8 are each independently preferably an alkyl group having 3 to 5 carbon atoms, more preferably a branched alkyl group having 3 to 5 carbon atoms, and still more preferably a group represented by the following formula:

[Chemical 10]

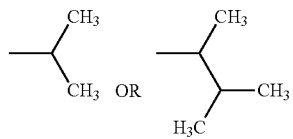

Preferred examples of the compound A include compounds A-1 to A-4 below. Among others, A-1 and A-2 are preferable from the viewpoint of further improving the potential stability during repeated use.

[Chemical 11]

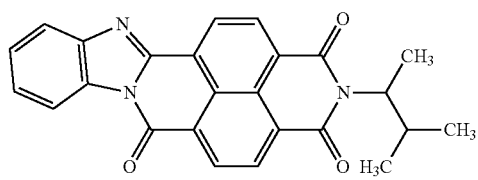

A-1

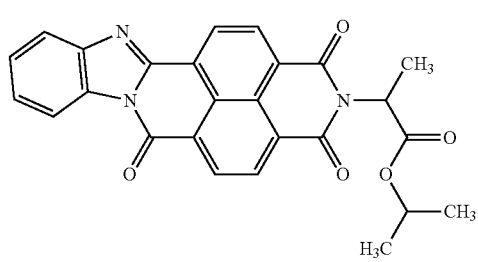

A-2

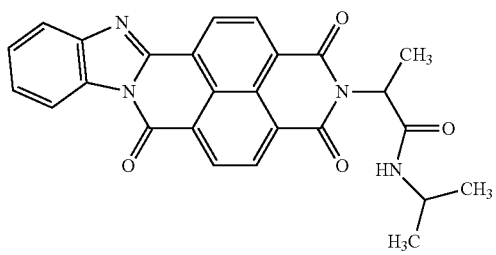

A-3

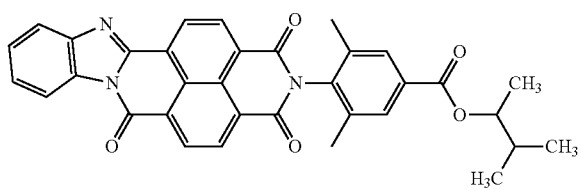

A-4

The compound A may be a synthetic product or a commercially available product. In the case of a synthetic product, the synthesis method is not particularly limited, and known organic synthesis methods combined as appropriate may be used. Specifically, the compound can be synthesized by the methods described in Examples.

The content of the compound A in the undercoat layer is not particularly limited but, from the viewpoint of further improving effects of the present invention, with respect to 100 parts by mass of the binder resin, the content of the compound A is preferably 0.5 to 100 parts by mass, more preferably 1 to 30 parts by mass, and still more preferably 5 to 15 parts by mass.

[Metal Oxide Particles]

From the viewpoint of further improving effects of the present invention, in the photoconductor of the present invention, the undercoat layer preferably further contains metal oxide particles in addition to the compound A described above. The metal oxide particles may be of a single type or of two or more types.

The type of the metal oxide is not particularly limited, and examples thereof include metal oxides such as titanium oxide, zinc oxide, alumina (aluminum oxide), silica (silicon oxide), tin oxide, antimony oxide, indium oxide, bismuth oxide, magnesium oxide, lead oxide, tantalum oxide, yttrium oxide, cobalt oxide, copper oxide, manganese oxide, selenium oxide, iron oxide, zirconium oxide, germanium oxide, niobium oxide, molybdenum oxide, and vanadium oxide, and tin-doped indium oxide, and antimony-doped tin oxide and zirconium oxide. Among others, from the viewpoint of further improving effect of the present invention, the metal oxide is preferably at least one selected from the group consisting of titanium oxide, zinc oxide, tin oxide, and aluminum oxide. Furthermore, from the viewpoint of further improving the potential stability during repeated use, the metal oxide is preferably titanium oxide.

The average particle size (number average primary particle size) of metal oxide particles is not particularly limited, but is preferably 10 to 100 nm, and more preferably 20 nm to less than 50 n. The average particle size of metal oxide particles can be determined by photographing sample particles with a scanning electron microscope at a magnification of 100,000 times, binarizing the sample particles using an automatic image processing analyzer, calculating horizontal Feret diameters of 100 particles randomly selected, and obtaining their average value (number average primary particle size) as an "average particle size". The horizontal Feret diameter herein refers to the length of a side parallel to the x-axis of a circumscribed rectangle obtained when an image of sample particles is binarized.

The content of the metal oxide particles (surface-treated metal oxide particles if surface-treated) in the undercoat layer is not particularly limited, but the content is preferably 200 to 3,000 parts by mass, more preferably 500 to 2,000 parts by mass, and still more preferably 1,000 to 1,500 parts by mass, with respect to 100 parts by mass of the binder resin. Note that, in the case where two or more types of metal oxide particles are used in combination, the total content thereof is preferably within the ranges described above.

The metal oxide particles are preferably surface-treated (surface-modified) with a silane coupling agent. In particular, it is preferable that the metal oxide particles are surface-coated with silica or alumina as described above, and then further surface-treated with a silane coupling agent. The metal oxide particles are preferably surface-treated with a silane coupling agent because the coating solution used in the manufacturing process can be better dispersed. Furthermore, the surface treatment is preferably performed because the number of hydrophilic group sites on the surface of the metal oxide particles is decreased, and variation in electrical characteristics of the photoconductor caused by difference in temperature and humidity in the operational environment is reduced.

Examples of a silane coupling agent that may be used include, without particular limitation, methyltrimethoxysilane, n-butyltrimethoxysilane, n-hexyltrimethoxysilane, dimethyldimethoxysilane, N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, N-phenyl-3-aminopropyltrimethoxysilane, and a (meth)acryloyl group-containing silane coupling agent (specifically, the compounds represented by the following formulas S-1 to S-42). One of the above silane coupling agents may be used alone or two or more thereof may be used in combination.

[Chemical 12]

S-1: $CH_2\!\!=\!\!CHSi(CH_3)(OCH_3)_2$
S-2: $CH_2\!\!=\!\!CHSi(OCH_3)_3$
S-3: $CH_2\!\!=\!\!CHSiCl_3$
S-4: $CH_2\!\!=\!\!CHCOO(CH_2)_2Si(CH_3)(OCH_3)_2$
S-5: $CH_2\!\!=\!\!CHCOO(CH_2)_2Si(OCH_3)_3$
S-6: $CH_2\!\!=\!\!CHCOO(CH_2)_2Si(OC_2H_5)(OCH_3)_2$
S-7: $CH_2\!\!=\!\!CHCOO(CH_2)_3Si(OCH_3)_3$
S-8: $CH_2\!\!=\!\!CHCOO(CH_2)_2Si(CH_3)Cl_2$
S-9: $CH_2\!\!=\!\!CHCOO(CH_2)_2SiCl_3$
S-10: $CH_2\!\!=\!\!CHCOO(CH_2)_3Si(CH_3)Cl_2$
S-11: $CH_2\!\!=\!\!CHCOO(CH_2)_3SiCl_3$
S-12: $CH_2\!\!=\!\!C(CH_3)COO(CH_2)_2Si(CH_3)(OCH_3)_2$
S-13: $CH_2\!\!=\!\!C(CH_3)COO(CH_2)_2Si(OCH_3)_3$
S-14: $CH_2\!\!=\!\!C(CH_3)COO(CH_2)_3Si(CH_3)(OCH_3)_2$
S-15: $CH_2\!\!=\!\!C(CH_3)COO(CH_2)_3Si(OCH_3)_3$
S-16: $CH_2\!\!=\!\!C(CH_3)COO(CH_2)_2Si(CH_3)Cl_2$
S-17: $CH_2\!\!=\!\!C(CH_3)COO(CH_2)_2SiCl_3$
S-18: $CH_2\!\!=\!\!C(CH_3)COO(CH_2)_3Si(CH_3)Cl_2$
S-19: $CH_2\!\!=\!\!C(CH_3)COO(CH_2)_3SiCl_3$
S-20: $CH_2\!\!=\!\!CHSi(C_2H_5)(OCH_3)_2$
S-21: $CH_2\!\!=\!\!C(CH_3)Si(OCH_3)_3$
S-22: $CH_2\!\!=\!\!C(CH_3)Si(OC_2H_6)_3$
S-23: $CH_2\!\!=\!\!CHSi(OCH_3)_3$
S-24: $CH_2\!\!=\!\!C(CH_3)Si(CH_3)(OCH_3)_2$
S-25: $CH_2\!\!=\!\!CHSi(CH_3)Cl_2$
S-26: $CH_2\!\!=\!\!CHCOOSi(OCH_3)_3$

S-27: $CH_2$=$CHCOOSi(OC_2H_6)_3$
S-28: $CH_2$=$C(CH_3)COOSi(OCH_3)_3$
S-29: $CH_2$=$C(CH_3)COOSi(OC_2H_6)_3$
S-30: $CH_2$=$C(CH_3)COO(CH_2)_3Si(OC_2H_5)_3$
S-31: $CH_2$=$CHCOO(CH_2)_2Si(CH_3)_2(OCH_3)$
S-32: $CH_2$=$CHCOO(CH_2)_2Si(CH_3)(OCOCH_3)_2$
S-33: $CH_2$=$CHCOO(CH_2)_2Si(CH_3)(ONHCH_3)_2$
S-34: $CH_2$=$CHCOO(CH_2)_2Si(CH_3)(OC_6H_5)_2$
S-35: $CH_2$=$CHCOO(CH_2)_2Si(C_{10}H_{21})(OCH_3)_2$
S-36: $CH_2$=$CHCOO(CH_2)_2Si(CH_2C_6H_5)(OCH_3)_2$
S-37: $(CH_3O)_2(CH_3)SiC_3H_6NHC_2H_4NH_2$
S-38: $(CH_3O)_3SiC_3H_6NHC_2H_4NH_2$
S-39: $(CH_3O)_3SiC_3H_5NH_2$
S-40: $(C_2H_5O)_3SiC_3H_6NH_2$
S-41: $(C_2H_5O)_3SiC_3H_6N$=$C(CH_3)(C_4H_9)$
S-42: $(CH_3O)_3SiC_3H_6NH$—$(C_6H_3)$

The metal oxide particles may be surface-treated with a silane coupling agent by using a known method. For example, as a wet process, metal oxide particles may be added to and mixed with a solution in which a silane coupling agent is dispersed in water or in an organic solvent and the mixture may be stirred, or the metal oxide particles may be dispersed in water or in an organic solvent and a silane coupling agent may be added and adhered to the metal oxide particles. Then, the resultant solution may be filtered and dried, and the obtained metal oxide particles may be annealed (baked) to complete the surface treatment.

The mixing and stirring temperature during a wet process is preferably about 30 to 150° C., and more preferably 40 to 60° C. The mixing and stirring time is preferably 0.5 to 10 hours, and more preferably 1 to 5 hours. The annealing temperature may be, for example, 100 to 220° C., preferably 110 to 150° C. The annealing time is preferably 0.5 to 10 hours, and more preferably 1 to 5 hours.

The amount of a silane coupling agent to be used is not particularly limited, but may be 0.1 to 20 parts by mass, more preferably 1 to 15 parts by mass, and still more preferably 1 to 10 parts by mass, with respect to 100 parts by mass of the metal oxide particles prior to the surface treatment. The amount of water or an organic solvent to be added is not particularly limited, but may be 500 to 3,000 parts by mass, and more preferably 1,000 to 2,000 parts by mass, with respect to 100 parts by mass of the metal oxide particles prior to the surface treatment.

If the amount of each silane coupling agent is within the above ranges, the metal oxide particles can be surface-treated to a sufficient degree. As a result, the hole blocking property of the undercoat layer can be maintained and the occurrence of image defects such as black spots and fogging can be sufficiently suppressed. In addition, the amount is preferred because a uniform coating is applied to the surface of metal oxide particles.

Whether the metal oxide particles are surface-treated with a silane coupling agent can be confirmed by performing an inorganic analysis on the surface of the metal oxide particles using transmission energy dispersive X-ray spectroscopy (TEM-EDX) or wavelength dispersive X-ray fluorescence analysis (WDX).

[Binder Resin]

The undercoat layer included in the photoconductor of the present invention preferably further contains a binder resin in addition to the compound A and the metal oxide particles described above.

The binder resin used for the undercoat layer is not particularly limited, and examples of the binder resin include polyamide resin, casein, polyvinyl alcohol resin, nitrocellulose, ethylene-acrylic acid copolymer, vinyl chloride resin, vinyl acetate resin, vinyl chloride-vinyl acetate copolymer resin, polyurethane resin, and gelatin. One of these resins may be used alone or two or more thereof may be used in combination. Among others, vinyl chloride-vinyl acetate copolymer resin is particularly preferred from the viewpoint of further improving effects of the present invention. The binder resin to be used may be a synthetic product or a commercially available product.

[Cross-Linking Agent]

During formation of the undercoat layer, it is preferable to use a cross-linking agent. By using a cross-linking agent, a cross-linking structure is formed in the undercoat layer, and resultingly effects of the present invention can be further improved. Accordingly, in one embodiment of the present invention, the coating solution for forming the undercoat layer contains a cross-linking agent.

A known cross-linking agent may be used as the cross-linking agent without particular limitation, as long as the cross-linking agent has reactivity with other components (the compound A, the metal oxide particles, the binder resin, and so on) contained in the undercoat layer. Among others, an isocyanate-based cross-linking agent is preferred from the viewpoint of reactivity.

Examples of the isocyanate-based cross-linking agent include aliphatic diisocyanates such as hexamethylene diisocyanate (HDI); aromatic diisocyanates such as tolylene diisocyanate, xylylene diisocyanate, and diphenylmethane diisocyanate; alicyclic diisocyanates such as isophorone diisocyanate; and polyisocyanates such as an adduct of a diisocyanate compound and a polyol compound such as trimethylolpropane, and a biuret or isocyanurate of a diisocyanate compound, where a blocked product (blocked isocyanate) of the polyisocyanate is preferred. Examples of a blocking agent include phenol, ε-caprolactam, methyl ethyl ketoxime, and an active methylene compound, and a blocking agent may be appropriately selected in accordance with the heat treatment temperature.

The isocyanate-based cross-linking agent to be used may be a synthetic product or a commercially available product. Examples of the commercially available product include Coronate (registered trademark, the same applies to the following) L, Coronate HL, Coronate HX, Coronate 2030, Coronate 2031, Coronate 2507, Coronate 2554, and Coronate BI-301 manufactured by Tosoh Corporation and DURANATE (trademark, the same applies to the following) 24A-100, DURANATE TPA-100, DURANATE TKA-100, DURANATE MF-K60B, DURANATE SBB-70P, DURANATE SBN-70D, DURANATE MF-B60B, DURANATE 17B-60P, DURANATE TPA-B80E, and DURANATE E402-B80B manufactured by Asahi Kasei Corporation.

The amount of the cross-linking agent used in the coating solution for forming the undercoat layer is not particularly limited, but may be, for example, preferably 50 to 300 parts by mass with respect to 100 parts by mass of the binder resin.

[Other Components]

The undercoat layer may further contain a known additive in addition to the compound A, the metal oxide particles, the binder resin, and the cross-linking agent to the extent that effects of the present invention are not impaired.

[Method for Forming Undercoat Layer]

The method for forming the undercoat layer is not particularly limited, and the undercoat layer can be formed by, for example, dissolving or dispersing the compound A and, if necessary, the metal oxide particles, the binder resin, the cross-linking agent, and other additives in a solvent to prepare a coating solution for forming the undercoat layer, applying the coating solution for forming the undercoat layer on the surface of the conductive support, and then drying the coating solution.

The solvent used for preparing the coating solution for forming the undercoat layer is not particularly limited as long as the solvent can dissolve or disperse the components of the undercoat layer. However, in the case of using a cross-linking agent, a solvent having lower reactivity with the cross-linking agent is preferred. For example, in the case of using an isocyanate-based cross-linking agent, a ketone-based solvent such as 2-butanone or cyclohexanone is preferred.

During preparation of the coating solution for forming the undercoat layer, an ultrasonic dispersing machine, a bead mill, a ball mill, a sand mill, a homomixer, or the like can be used as a disperser.

The concentration of the binder resin in the coating solution for forming the undercoat layer varies depending on the thickness of the undercoat layer and the coating method, but the amount of the solvent to be used may be, for example, preferably 100 to 3,000 parts by mass, and more preferably 500 to 2,000 parts by mass, with respect to 100 parts by mass of the binder resin.

The method for applying the coating solution for forming the undercoat layer is not particularly limited, and examples of the method include a dip coating method, a spray coating method, a spinner coating method, a bead coating method, a blade coating method, a beam coating method, and a slide hopper method.

As the drying method, a known drying method can be appropriately selected in accordance with the type of the solvent and the thickness of the undercoat layer to be formed, but heat drying is preferred. The heating conditions are not particularly limited, and the heating may be performed, for example, at 100 to 150° C. for 10 to 90 minutes.

The undercoat layer has a thickness of, for example, 0.5 to 30 μm. Furthermore, from the viewpoint of further suppressing the occurrence of image memory, the thickness of the undercoat layer is more preferably 1 to 25 μm, and still more preferably 5 to 20 μm.

<Photosensitive Layer>

The photosensitive layer included in the photoconductor of the present invention is a layer for forming an electrostatic latent image on the surface of the photoconductor through exposure, the electrostatic latent image corresponding to a desired image. In the photoconductor of the present invention, the photosensitive layer may contain the compound A described above.

The photosensitive layer may have, for example, a configuration in which a charge generation layer containing a charge generation material and a charge transport layer containing a charge transport material are laminated (also referred to as a "laminated type" herein). Alternatively, the photosensitive layer may have a configuration in which the charge generation material and the charge transport material are contained in the same layer (also referred to as a "single-layer type" herein). However, from the viewpoint of controlling electrostatic characteristics of the photoconductor, the photosensitive layer is preferably of a laminated type. That is, in the photoconductor according to one embodiment of the present invention, the photosensitive layer includes a charge generation layer and a charge transport layer, and at least the undercoat layer, the charge generation layer, and the charge transport layer are laminated in the order mentioned on the conductive support.

The following describes the charge generation layer and the charge transport layer included in the laminated type photosensitive layer.

[Charge Generation Layer]

The charge generation layer has a function of generating charges through exposure. The charge generation layer preferably contains a charge generation material and a binder resin, and may further contain the above-described compound A in addition thereto.

(Charge Generation Material)

Examples of the charge generation material include azo materials such as sudan red and diane blue; quinone compounds such as pyrenequinone and anthanthrone; quinocyanine compounds; perylene compounds; indigo compounds such as indigo and thioindigo; pyranthrone or diphthaloylpyrene polycyclic quinone compounds; and phthalocyanine compounds. The charge generation material may be of a single type or of two or more types.

The phthalocyanine compound may or may not have a central metal. Examples of the central metal include Ti, Fe, V, Ga, Si, Pb, Al, Zn, and Mg. The central metal may be of a single type or of two or more types. From the viewpoint of further improving effects of the present invention, the phthalocyanine compound is preferably a gallium phthalocyanine compound having Ga as a central metal or a titanyl phthalocyanine compound having Ti as a central metal, and is more preferably a titanyl phthalocyanine compound. That is, in the photoconductor according to one embodiment of the present invention, the charge generation layer contains a titanyl phthalocyanine compound.

Examples of the titanyl phthalocyanine compound include those having a crystal form such as Y-type, A-type (D-type), and B-type (α-type), and Y-type titanyl phthalocyanine or B-type titanyl phthalocyanine is preferred. Y-type titanyl phthalocyanine has a maximum diffraction peak at least at a Bragg angle (2θ±0.2) of 27.3° in an X-ray diffraction spectrum with a CuKα ray. B-type titanyl phthalocyanine has a maximum diffraction peak at least at a Bragg angle (2θ±0.2) of 28.6° in an X-ray diffraction spectrum with a CuKα ray. The titanyl phthalocyanine compound to be used may be a synthetic product or a commercially available product. In the case of a synthetic product, the synthesis method is not particularly limited. For example, the synthetic product can be synthesized by referring to, for example, JP 2006-154749 A (Y-type titanyl phthalocyanine) and JP 2009-037058 A (B-type titanyl phthalocyanine).

As the gallium phthalocyanine compound, hydroxygallium phthalocyanine, for example, may be used. Hydroxygallium phthalocyanine has a maximum diffraction peak at least at a position of a Bragg angle (2θ±0.2) of 28.1° in a Cu-Kα characteristic X-ray diffraction spectrum. The gallium phthalocyanine compound to be used may be a synthetic product or a commercially available product. In the case of a synthetic product, the synthesis method is not particularly limited. For example, the synthetic product can be synthesized by referring to, for example, JP 2002-235014 A.

The content of the charge generation material in the charge generation layer is not particularly limited, but is preferably 20 to 600 parts by mass, and more preferably 50 to 500 parts by mass, with respect to 100 parts by mass of the binder resin.

(Binder Resin)

The binder resin used for the charge generation layer is not particularly limited, and examples thereof include known resins such as formal resin, butyral resin, silicone resin, silicone-modified butyral resin, phenoxy resin, polystyrene resin, polyethylene resin, polypropylene resin, acrylic resin, methacrylic resin, vinyl chloride resin, vinyl acetate resin, polyvinyl butyral resin, epoxy resin, polyurethane resin, phenolic resin, polyester resin, alkyd resin, polycarbonate resin, melamine resin, and copolymer resin containing two or more of these resins (for example, vinyl chloride-vinyl acetate copolymer resin or vinyl chloride-vinyl acetate-maleic anhydride copolymer resin), and polyvinyl carbazole resin. One of these resins may be used alone or two or more thereof may be used in combination. Among others, polyvinyl butyral resin is preferred.

The charge generation layer may further contain a known additive in addition to the charge generation material, the binder resin, and the compound A described above.

The thickness of the charge generation layer is not particularly limited, but is preferably 0.05 to 2.0 μm.

(Method for Forming Charge Generation Layer)

The method for forming the charge generation layer is not particularly limited, and the charge generation layer can be formed by, for example, dissolving or dispersing the above-described components including the charge generation material, the binder resin, the compound A, and an additive in a solvent to prepare a coating solution for forming the charge generation layer, applying the coating solution for forming the charge generation layer on the undercoat layer, and then drying the coating solution.

The solvent used for preparing the coating solution for forming the charge generation layer can be appropriately selected in accordance with the dispersibility and the coating properties of the above components, and examples of the solvent include methyl ethyl ketone, methyl isopropyl ketone, methyl isobutyl ketone, cyclohexanone, acetophenone, tetrahydrofuran, dioxolane, diethylene glycol dimethyl ether, 2-methoxyethanol, 2-ethoxyethanol, butanol, ethyl acetate, t-butyl acetate, toluene, chlorobenzene, dichloroethane, trichloroethane, and 4-methoxy-4-methyl-2-pentanone (MMP). One of these resins may be used alone or two or more thereof may be used in combination.

During preparation of the coating solution for forming the charge generation layer, an ultrasonic dispersing machine, a bead mill, a ball mill, a sand mill, a homomixer, or the like can be used as a disperser.

The method for applying the coating solution for forming the charge generation layer is not particularly limited, and examples of the method include a dip coating method, a spray coating method, a spinner coating method, a bead coating method, a blade coating method, a beam coating method, and a slide hopper method.

As the drying method, a known drying method can be appropriately selected in accordance with the type of the solvent and the thickness of the undercoat layer to be formed, but heat drying is preferred. The heating conditions are not particularly limited, and the heating may be performed, for example, at room temperature (25° C.) to 150° C. for 10 to 90 minutes.

The concentration of the binder resin in the coating solution for forming the charge generation layer varies depending on the thickness of the charge generation layer and the coating method, but the amount of the solvent to be used may be, for example, preferably 1,000 to 20,000 parts by mass with respect to 100 parts by mass of the binder resin.

[Charge Transport Layer]

The charge transport layer has a function of transporting charges (holes) generated through exposure to the surface of the photoconductor. The charge transport layer preferably contains a charge transport material and a binder resin, and may further contain the above-described compound A in addition thereto.

(Charge Transport Material)

From the viewpoint of further improving effects of the present invention, the charge transport layer preferably contains, as the charge transport material, at least one selected from the group consisting of compounds represented by the formulas 1 to 4 below.

[Chemical 13]

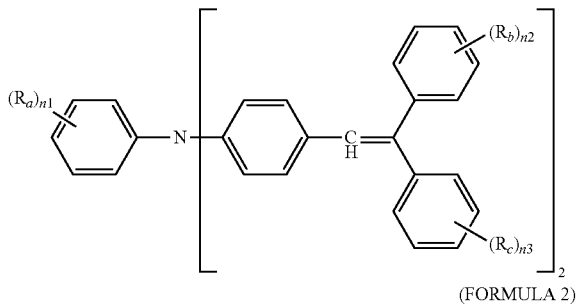

(FORMULA 1)

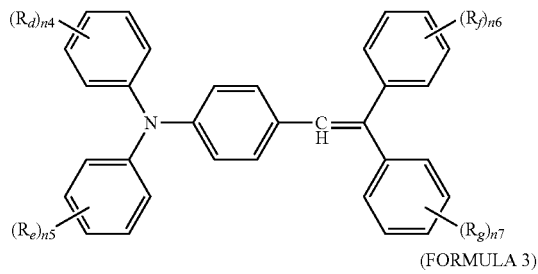

(FORMULA 2)

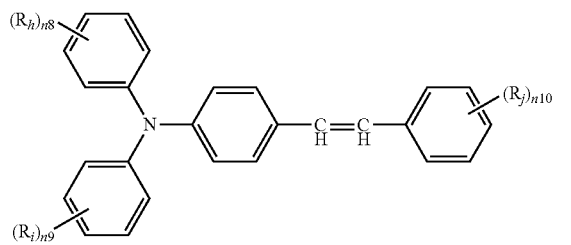

(FORMULA 3)

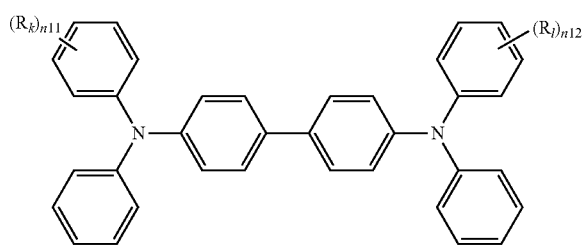

(FORMULA 4)

In the formulas 1 to 4 above, $R_a$ to $R_l$ are each independently an alkyl group having 1 to 3 carbon atoms, an alkoxy group having 1 to 3 carbon atoms, or a halogen atom, and n1 to n12 are each independently an integer of 0 to 5.

Examples of the alkoxy group having 1 to 3 carbon atoms include a methoxy group, an ethoxy group, and an n-propoxy group.

Examples of the halogen atom include a fluorine atom, a chlorine atom, a bromine atom, and an iodine atom.

In the formulas 1 to 4 above, $R_a$ to $R_1$ are preferably each independently a methyl group or a methoxy group.

Preferred examples of the charge transport material include CTM-1 to CTM-4 shown below. In the examples described later, CTM-1 to CTM-4 shown below were used as charge transport materials.

[Chemical 14]

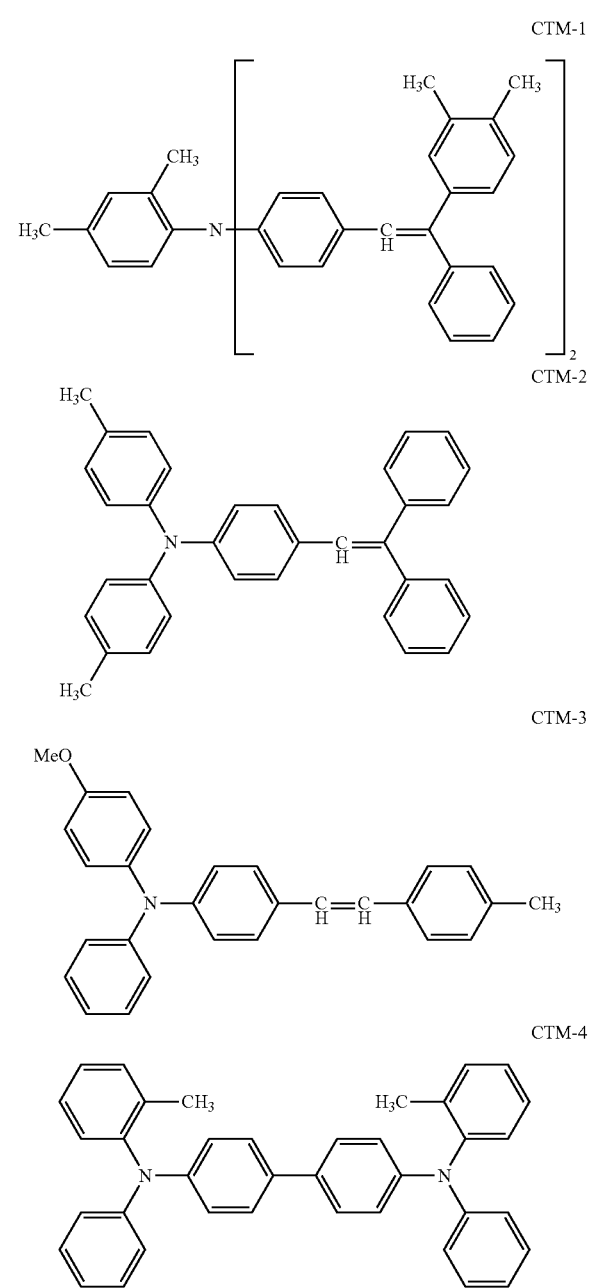

Each of the compounds represented by the formulas 1 to 4 above may be a synthetic product or a commercially available product. In the case of a synthetic product, the synthesis method is not particularly limited, and known organic synthesis methods combined as appropriate may be used. Specifically, the compounds can be synthesized with reference to the known reaction formulas 1 to 4 below.

REACTION FORMULA 1 (IN THE CASE OF CTM-1)

[Chemical 15]

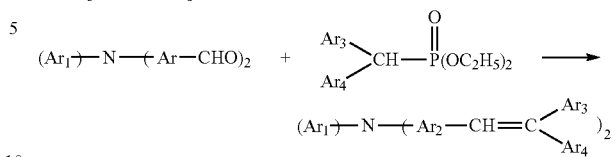

REACTION FORMULA 2 (IN THE CASE OF CTM-2)

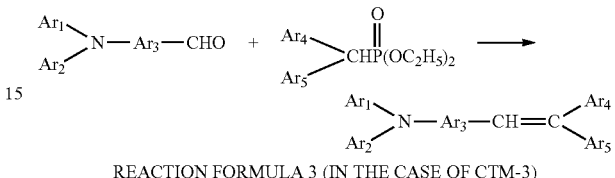

REACTION FORMULA 3 (IN THE CASE OF CTM-3)

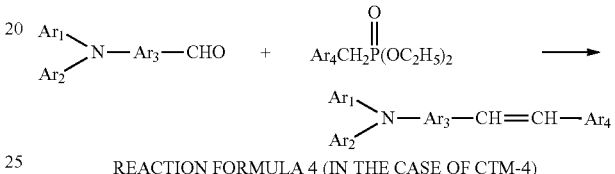

REACTION FORMULA 4 (IN THE CASE OF CTM-4)

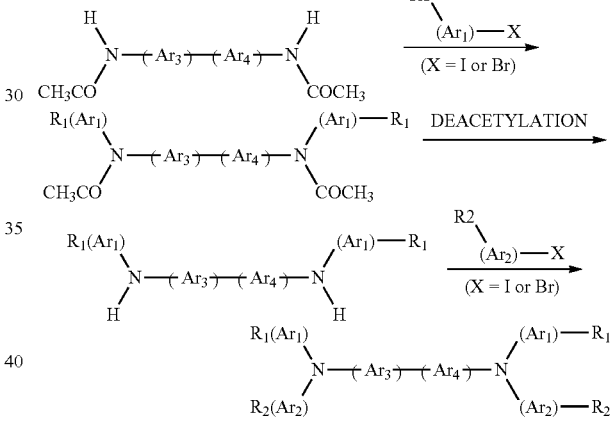

The content of the charge transport material in the charge transport layer is not particularly limited, but is preferably within the range of 10 to 200 parts by mass with respect to 100 parts by mass of the binder resin used in the charge transport layer.

(Binder Resin)

The binder resin used for the charge transport layer is not particularly limited, and examples of the binder resin include known resins including insulative resins such as polystyrene resin, acrylic resin, methacrylic resin, vinyl chloride resin, vinyl acetate resin, polyvinyl butyral resin, epoxy resin, polyurethane resin, phenolic resin, polyester resin, alkyd resin, polycarbonate resin, silicone resin, melamine resin, and copolymer resin having two or more of the repeat units of these resins; and organic semiconductors such as poly-N-vinylcarbazole. One of these resins may be used alone or two or more thereof may be used in combination. Among others, polycarbonate resin is preferred from the viewpoint of further improving effects of the present invention.

The charge transport layer may further contain a known additive in addition to the charge transport material, the binder resin, and the compound A described above. Examples of a known additive include an antioxidant and a silicone oil.

Examples of the antioxidant include dibutylhydroxytoluene (BHT) and butylhydroxyanisole (BHA).

Examples of the silicone oil include straight silicone oils such as dimethyl silicone oil, methylphenyl silicone oil, and methyl hydrogen silicone oil; and modified silicone oils such as amino modified silicone oil, epoxy modified silicone oil, carboxyl modified silicone oil, carbinol modified silicone oil, methacryl modified silicone oil, mercapto modified silicone oil, heterofunctional group modified silicone oil, polyether modified silicone oil, methylstyryl modified silicone oil, hydrophilic specific modified silicone oil, higher alkoxy modified silicone oil, higher fatty acid containing modified silicone oil, and fluorine modified silicone oil.

The thickness of the charge transport layer is not particularly limited, but is preferably 10 to 40 μm.

(Method for Forming Charge Transport Layer)

The method for forming the charge transport layer is not particularly limited, and the charge transport layer can be formed by, for example, dissolving or dispersing the above-described components including the charge transport material, the binder resin, the compound A, and an additive in a solvent to prepare a coating solution for forming the charge transport layer, applying the coating solution for forming the charge transport layer on the charge generation layer, and then heating or drying the coating solution.

The solvent used for preparing the coating solution for forming the charge transport layer can be appropriately selected in accordance with the dispersibility and the coating properties of the above components, and examples of the solvent include methyl ethyl ketone, methyl isopropyl ketone, methyl isobutyl ketone, cyclohexanone, acetophenone, tetrahydrofuran, dioxolane, diethylene glycol dimethyl ether, 2-methoxyethanol, 2-ethoxyethanol, butanol, ethyl acetate, t-butyl acetate, toluene, chlorobenzene, dichloroethane, trichloroethane, and 4-methoxy-4-methyl-2-pentanone. One of these resins may be used alone or two or more thereof may be used in combination.

During preparation of the coating solution for forming the charge transport layer, an ultrasonic dispersing machine, a bead mill, a ball mill, a sand mill, a homomixer, or the like can be used as a disperser.

The method for applying the coating solution for forming the charge transport layer is not particularly limited, and examples of the method include a dip coating method, a spray coating method, a spinner coating method, a bead coating method, a blade coating method, a beam coating method, and a slide hopper method.

As the drying method, a known drying method can be appropriately selected in accordance with the type of the solvent and the thickness of the undercoat layer to be formed, but heat drying is preferred. The heating conditions are not particularly limited, and the heating may be performed, for example, at 100 to 150° C. for 10 to 120 minutes.

The concentration of the binder resin in the coating solution for forming the charge transport layer varies depending on the thickness of the charge transport layer and the coating method, but the amount of the solvent to be used may be, for example, preferably 100 to 3,000 parts by mass with respect to 100 parts by mass of the binder resin.

[Single-Layer Type Photosensitive Layer]

The single-layer type photosensitive layer preferably contains a charge generation material, a charge transport material, and a binder resin, and may further contain the above-described compound A in addition thereto.

Examples of the charge generation material preferably used for the single-layer type photosensitive layer include the charge generation materials listed in the section entitled [Charge generation layer] above. The content of the charge generation material in the single-layer type photosensitive layer is not particularly limited, but is preferably 0.05 to 5 parts by mass with respect to 100 parts by mass of the binder resin.

Examples of the charge transport material preferably used for the single-layer type photosensitive layer include the charge transport materials listed in the section entitled [Charge transport layer] above. The content of the charge transport material in the single-layer type photosensitive layer is not particularly limited, but is preferably 10 to 100 parts by mass with respect to 100 parts by mass of the binder resin.

Examples of the binder resin preferably used for the single-layer type photosensitive layer include the binder resins listed in the section entitled [Charge transport layer] above.

The single-layer type photosensitive layer may further contain a known additive in addition to the charge generation material, the charge transport material, the binder resin, and the compound A described above. Examples of a known additive include an antioxidant and a silicone oil.

The thickness of the single-layer type photosensitive layer is not particularly limited, but is preferably 10 to 50 μm.

(Method for Forming Single-Layer Type Photosensitive Layer)

The method for forming the single-layer type photosensitive layer is not particularly limited, and the single-layer type photosensitive layer can be formed by, for example, dissolving or dispersing the above-described components including the charge generation material, the charge transport material, the binder resin, the compound A, and an additive in a solvent to prepare a coating solution for forming the photosensitive layer, applying the coating solution for forming the photosensitive layer on the undercoat layer, and then drying the coating solution.

Preferred embodiments of the solvent used in the coating solution for forming the photosensitive layer, the disperser for preparing the coating solution, the method for coating the coating solution, and the drying method subsequent to the coating are similar to those in the section (Method for forming charge transport layer) above.

The concentration of the binder resin in the coating solution for forming the photosensitive layer varies depending on the thickness of the photosensitive layer and the coating method, but the amount of the solvent to be used may be, for example, preferably 100 to 3,000 parts by mass with respect to 100 parts by mass of the binder resin.

[Other Layers]

The electrophotographic photoconductor of the present invention may further include a layer on the conductive support other than the undercoat layer and the photosensitive layer described above. For example, a protective layer may be disposed on the photosensitive layer to protect the photosensitive layer. Components of the protective layer and the method for forming the protective layer are not particularly limited.

<Electrophotographic Image Forming Apparatus and Method for Forming Electrophotographic Images>

An electrophotographic image can be formed by installing the electrophotographic photoconductor of the present invention in an electrophotographic image forming apparatus. The electrophotographic image forming apparatus preferably includes a charger, an exposure unit, a developer, and a transferrer.

Figure 2:
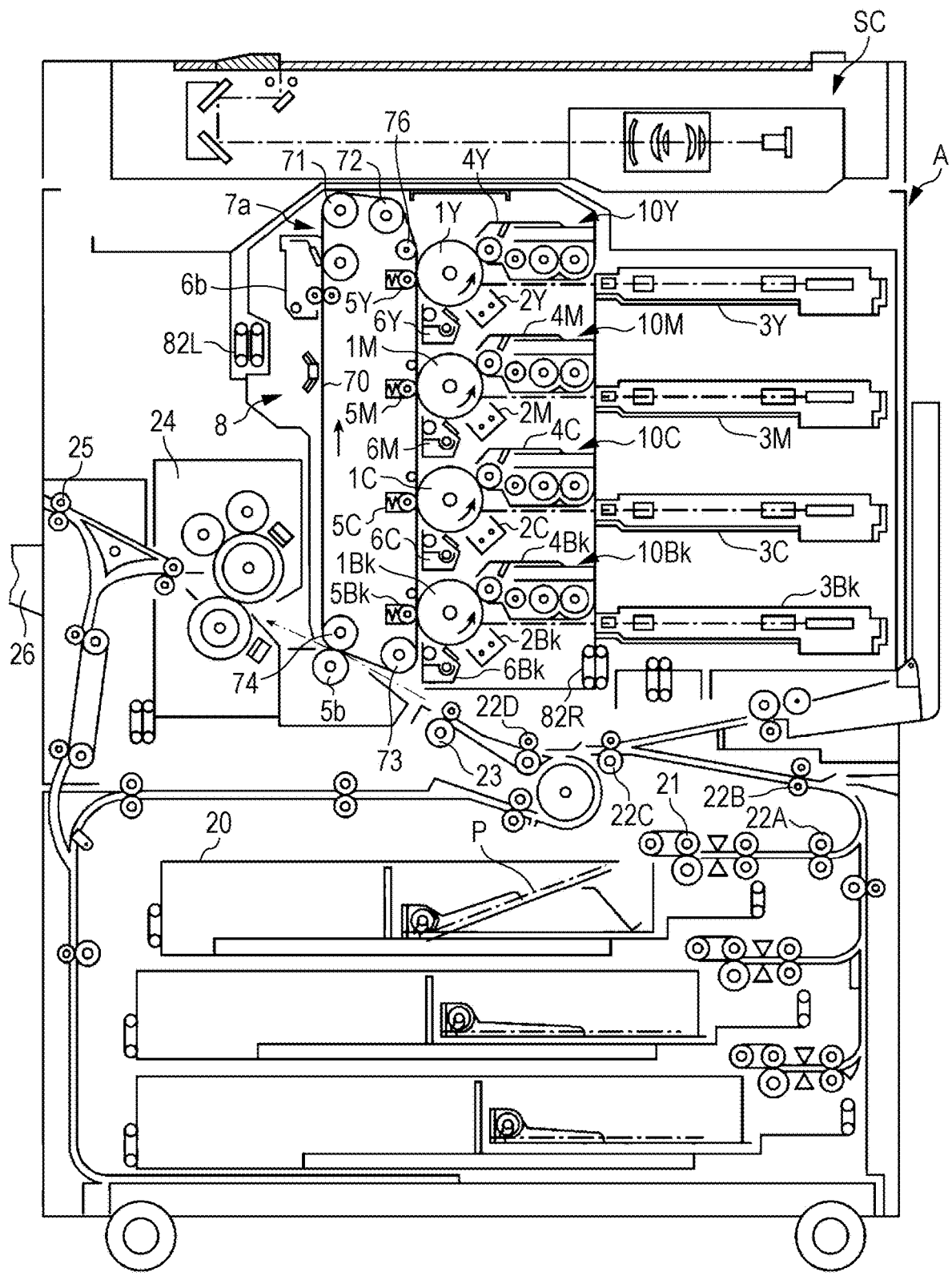
FIG. 2 is a schematic cross-sectional view illustrating an example of an electrophotographic image forming apparatus according to an embodiment of the present invention.

The following describes an electrophotographic image forming apparatus that includes the electrophotographic photoconductor of the present invention and a method for forming an electrophotographic image. FIG. 2 is a cross-sectional configuration diagram illustrating a full-color electrophotographic image forming apparatus, which is an example of an embodiment of the present invention. Note that the following description assumes that the electrophotographic photoconductor of the present invention is used as photoconductors 1Y, 1M, 1C and 1Bk.

This color image forming apparatus is called a tandem type color image forming apparatus and includes four sets of image forming units 10Y, 10M, 10C, and 10Bk, an endless belt-shaped intermediate transfer unit 7a, a sheet feeder 21, and a fixer 24. An original document image scanning device SC is disposed on top of a main body A of the image forming apparatus.

The image forming unit 10Y that forms a yellow image includes a charger 2Y, an exposure unit 3Y, a developer 4Y, a primary transfer roller 5Y, and a cleaner 6Y, which are arranged around a drum-shaped photoconductor 1Y serving as a first image carrier, the primary transfer roller 5Y serving as a primary transferrer. The image forming unit 10M that forms a magenta image includes a drum-shaped photoconductor 1M serving as a first image carrier, a charger 2M, an exposure unit 3M, a developer 4M, a primary transfer roller 5M serving as a primary transferrer, and a cleaner 6M. The image forming unit 10C that forms a cyan image includes a drum-shaped photoconductor 1C serving as a first image carrier, a charger 2C, an exposure unit 3C, a developer 4C, a primary transfer roller 5C serving as a primary transferrer, and a cleaner 6C. The image forming unit 10Bk that forms a black image includes a drum-shaped photoconductor 1Bk serving as a first image carrier, a charger 2Bk, an exposure unit 3Bk, a developer 4Bk, a primary transfer roller 5Bk serving as a primary transferrer, and a cleaner 6Bk.

The image forming units 10Y, 1GM, 10C, and 10Bk each have the same configuration except that colors of a toner image formed on the photoconductors 1Y, 1M, 1C, and 1Bk respectively are different, and thus the following describes the image forming unit 10Y in detail as an example.

The image forming unit 10Y, which includes the charger 2Y (hereinafter also referred to as a "charging device 2Y"), the exposure unit 3Y, the developer 4Y, and the cleaner 6Y disposed around the photoconductor 1Y being an image forming body, forms a yellow (Y) toner image on the photoconductor 1Y. In the present embodiment, at least the photoconductor 1Y, the charger 2Y, the developer 4Y, and the cleaner 6Y in the image forming unit 10Y are disposed so as to be integrated with one another.

The charger 2Y gives a uniform potential to the photoconductor 1Y. In the present embodiment, a corona discharge type charging device 2Y is used for the photoconductor 1Y.

The exposure unit 3Y performs exposure on the photoconductor 1Y to which a uniform potential is given by the charger 2Y, on the basis of an image signal (yellow), to form an electrostatic latent image corresponding to the yellow image. As an example of the exposure unit 3Y, a unit including an LED in which light emitting elements are arranged in an array along the axis direction of the photoconductor 1Y and an image forming element (trade name: Selfoc (registered trademark) lens), or a laser optical system may be used.

The developer 4Y includes, for example, a developing sleeve that contains a magnet and rotates while holding a developer, and also includes a voltage applying device that applies a DC and AC bias voltage or a DC or AC bias voltage between the photoconductor and the developing sleeve.

The endless belt-shaped intermediate transfer unit 7a includes an endless belt-shaped intermediate transfer member 70 as a second image carrier that is in a shape of a semiconductive endless belt, wound on a plurality of rollers, and circulatably held.

Color images formed in the image forming units 10Y, 10M, 10C, and 10Bk, respectively, are sequentially transferred onto the circulating endless belt-shaped intermediate transfer member 70 by the primary transfer rollers 5Y, 5M, 5C, and 5Bk serving as primary transferrers, thereby forming a synthesized color image. A transfer material P, which is a transfer material (a support carrying a final fixed image such as a plain paper or a transparent sheet) loaded in a paper feed cassette 20, is fed by a sheet feeder 21, and conveyed to a secondary transfer roller 5b serving as a secondary transferrer through a plurality of intermediate rollers 22A, 22B, 22C, and 22D and a registration roller 23, thereby achieving secondary transfer onto the transfer material P to collectively transfer the color image. The transfer material P on which the color image has been transferred is subjected to a fixing process performed by the fixer 24, sandwiched between paper output rollers 25, and placed on a paper output tray 26 outside the apparatus. Here, transfer supports for a toner image formed on the photoconductor such as the intermediate transfer member and the transfer material are collectively referred to as a transfer medium.

Besides, after the color image is transferred to the transfer material P by the secondary transfer roller 5b serving as a secondary transferrer, a cleaner 6b removes the toner remaining on the endless belt-shaped intermediate transfer member 70 that has self-stripped the transfer material P.

During the image forming process, the primary transfer roller 5Bk is always in contact with the photoconductor 1Bk. The other primary transfer rollers 5Y, 5M, and 5C are in contact with the corresponding photoconductors 1Y, 1M, and 1C, respectively, only for the period of image formation.

The secondary transfer roller 5b is in contact with the endless belt-shaped intermediate transfer member 70 only for the period of the secondary transfer while the transfer material P passes by the secondary transfer roller 5b.

Furthermore, a housing 8 is allowed to be pulled out from the main body A of the image forming apparatus via support rails 82L and 82R.

The housing 8 includes the image forming units 10Y, 10M, 10C, and 10Bk and the endless belt-shaped intermediate transfer unit 7a.

The image forming units 10Y, 10M, 10C, and 10Bk are arranged in tandem along the vertical direction. In the drawing, the endless belt-shaped intermediate transfer unit 7a is placed on the left side of the photoconductors 1Y, 1M, 1C and 1Bk. The endless belt-shaped intermediate transfer unit 7a includes the endless belt-shaped intermediate transfer member 70 that is circulatable and wound around rollers 71, 72, 76, 73, and 74, and also includes the primary transfer rollers 5Y, 5M, 5C, and 5Bk and the cleaner 6b.

[Neutralization Process]

Note that some conventional electrophotographic image forming apparatuses are configured such that a neutralization process can be performed by light irradiation subsequent to the transferring. Examples of the neutralizer (optical neutralizing device) used for the neutralization process include a fluorescent lamp and an LED. The light used for the neutralization process often has exposure energy equal to or greater than three times as high as the exposure energy of the exposure light.

However, an electrophotographic image forming apparatus employing the photoconductor of the present invention may have a configuration in which no neutralizer is included, because both long-term resistance against memory and prevention of image defects such as fogging can be provided without using such neutralizers. Thus, a configuration without an optical neutralization device is preferred because the image forming apparatus can achieve space saving and lower cost while the photoconductor suffers less optical damage.

[Process Cartridge]

The electrophotographic image forming apparatus of the present invention preferably includes a process cartridge (image forming unit) in which the electrophotographic photoconductor of the present invention is integrally combined with at least one of the above-mentioned charger (charging device), exposure unit (exposure device), developer (developing device), or cleaner (cleaning device), and the image forming unit is preferably allowed to be inserted and removed into/from (attachable to/detachable from) the main body of the electrophotographic image forming apparatus. Furthermore, the process cartridge (image forming unit) may be formed into a single image forming unit in which the photoconductor is integrally combined with at least one of the transferrer (transfer device) and the separator (separation device) as well as with the charger, the exposure unit, or the developer, so that the single image forming unit is attachable to/detachable from the main body of the apparatus through the use of guides such as rails disposed on the main body of the apparatus.

The electrophotographic image forming apparatus of the present invention can be generally applied to electrophotographic image forming apparatuses such as an electrophotographic copier, a laser printer, an LED printer, and a liquid crystal shutter printer and, furthermore, can be widely applied to apparatuses based on application of electrophotographic technology such as the apparatuses for display, recording, quick printing, plate making, and facsimile.

Embodiments to which the present invention is applicable are not limited to the foregoing embodiments, but can be modified as appropriate without departing from the gist of the present invention.

EXAMPLES

The present invention will now be described in detail with reference to examples, but the present invention is not limited to these examples. Note that the term or sign "parts" or "%" as used in the examples refers to "parts by mass" or "% by mass" unless otherwise specified.

Synthesis of Electron Transport Material

Production Example 1-1

A compound A-1 of the formula below was synthesized in accordance with the following procedure.

13.4 g (50 mmol) of 1,4,5,8-naphthalenetetracarboxylic dianhydride and 100 ml of N,N-dimethylformamide were placed in a four-necked flask and heated to reflux. A mixture of 4.3 g (50 mmol) of 1,2-dimethylpropylamide and 50 ml of DMF was added dropwise thereto while being stirred. After the dropwise addition, the mixture was heated to reflux for six hours. After completion of the reaction, the reaction vessel was cooled and the mixture was concentrated under reduced pressure. Toluene was added to the residue, and the resultant product was purified by silica gel column chromatography. The resultant product was further recrystallized with toluene/heptane to provide 5.3 g (yield: 31.4%) of a monoimide A represented by the following chemical formula.

[Chemical 16]

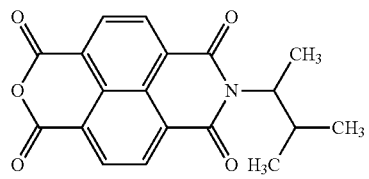

Monoimide A

In a four-necked flask, 3.37 g (10 mmol) of the above monoimide body A, 1.08 g (10 mmol) of o-phenylenediamine, 1.36 g (10 mmol) of zinc chloride, and 20 ml of 1,3-dimethyl-2-imidazolidinone were placed and heated to reflux for five hours. After completion of the reaction, 100 mL of methanol was added, and the precipitated crystals were filtered and then recrystallized with toluene/ethyl acetate to provide 3.31 g (yield: 80.8%) of the compound A-1.

[Chemical 17]

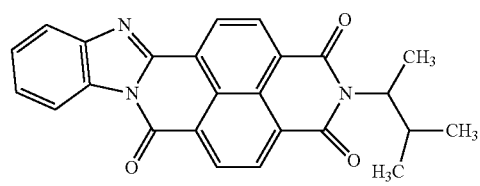

Production Example 1-2

In Production Example 1-1, the following compound A-2 was obtained in the same manner as in Production Example 1-1 except that $H_2N-CH(CH_3)COOCH(CH_3)_2$ was used instead of 1,2-dimethylpropylamide to provide a monoimide.

[Chemical 18]

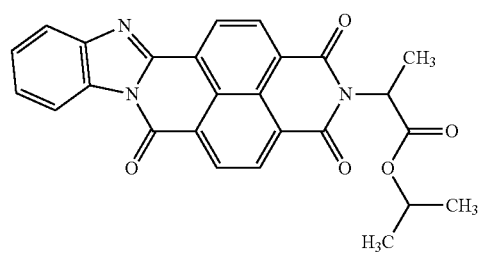

Production Example 1-3

In Production Example 1-1, the following compound A-3 was obtained in the same manner as in Production Example 1-1 except that H₂N—CH(CH₃)CONHCH(CH₃)₂ was used instead of 1,2-dimethylpropylamide to provide a monoimide.

[Chemical 19]

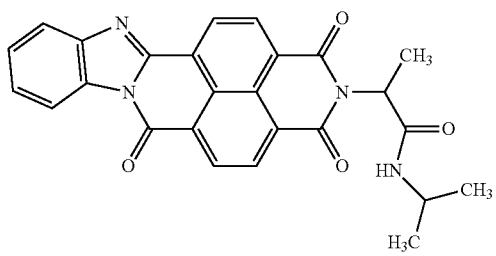

Production Example 1-4

A compound A'-1 of the following formula was synthesized with reference to JP 2007-199400 A.

[Chemical 20]

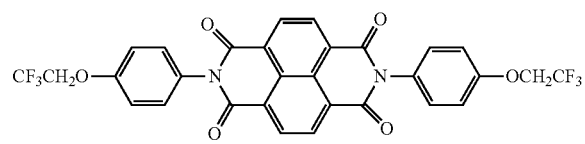

Production Example 1-5

A compound A'-2 of the following formula was synthesized with reference to JP 2007-108719 A.

[Chemical 21]

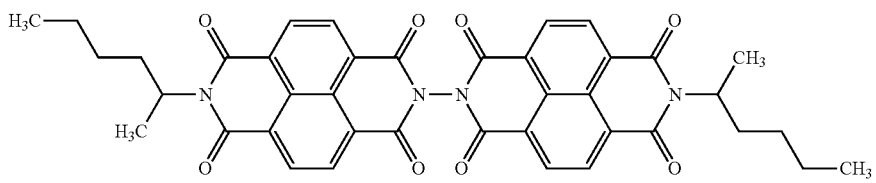

Production Example 1-6

A compound A'-3 of the following formula was synthesized with reference to JP 2005-10790 A.

[Chemical 22]

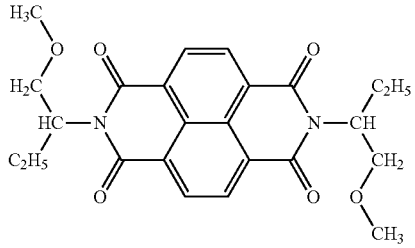

Production Example 1-7

A compound A'-4 of the following formula was synthesized with reference to JP 2016-95453 A.

[Chemical 23]

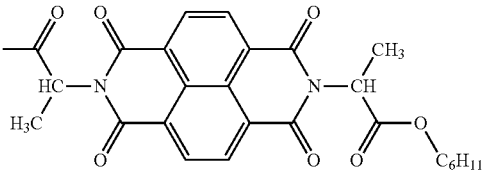

Preparation of Surface-Modified Metal Oxide Particles

Production Example 2-1

| | |
|---|---|
| Titanium oxide particles (SMT500SAS manufactured by Tayca Corporation) | 80 parts by mass |
| Silane coupling agent (KBM-503, 3-methacryloxypropyltrimethoxysilane manufactured by Shin-Etsu Chemical Co., Ltd.) | 1 part by mass |
| Toluene | 1,000 parts by mass |

The above components were mixed and stirred, toluene was removed therefrom, and the resulting product was heat-treated at 120° C. for one hour to provide surface-modified titanium oxide particles (average primary particle size: 35 nm, hereinafter also referred to as "metal oxide particles 1").

Production Example 2-2

In Production Example 2-1, surface-modified zinc oxide particles (average primary particle size: 35 nm, hereinafter also referred to as "metal oxide particles 2") were obtained in the same manner as in Production Example 2-1 except that zinc oxide particles (FINEX30 manufactured by Sakai Chemical Industry Co., Ltd.) were used instead of titanium oxide particles.

Production Example 2-3

In production Example 2-1, surface-modified tin oxide particles (hereinafter also referred to as "metal oxide particles 3") were obtained in the same manner as in Production Example 2-1 except that tin oxide particles (S-1 manufactured by Mitsubishi Materials Electronic Chemicals Co., Ltd) were used instead of titanium oxide particles.

Production Example 2-4

In Production Example 2-1, surface-modified aluminum oxide particles (average primary particle size: 31 n, hereinafter also referred to as "metal oxide particles 4") were obtained in the same manner as in Production Example 2-1 except that aluminum oxide particles (Nanotec Powder manufactured by C.I. Kasei Co., Ltd.) were used instead of titanium oxide particles.

Production Example 2-5

| | |
|---|---|
| Zinc oxide particles (MZ-300 manufactured by Tayca Corporation) | 500 parts by mass |
| Silane coupling agent (KBM-603 manufactured by Shin-Etsu Chemical Co., Ltd.) | 5 parts by mass |
| Toluene | 3,000 parts by mass |

The above components were mixed while being stirred, and then heat-treated at 120° C. for one hour to provide 5M metal oxide particles.

| | |
|---|---|
| Metal oxide particles 5M | 500 parts by mass |
| Alizarin | 10 parts by mass |
| Tetrahydrofuran (THF) | 3,000 parts by mass |

The above components were stirred and mixed while being heated at 40° C. for 10 hours. Then, the resultant product was filtered off and dried at 140° C. for one hour to provide surface-modified zinc oxide particles (average primary particle size 35 nm, hereinafter also referred to as "metal oxide particles 5").

Preparation of Photoconductor

Example 1

(1) Preparing Conductive Support

Cutting work was done on the surface of a cylindrical aluminum support having a diameter of 60 mm to produce a conductive support (φ60 mm×L 362 mm×t 1 mm) having a finely rough surface.

(2) Forming Undercoat Layer

| | |
|---|---|
| Metal oxide particles 1 | 100 parts by mass |
| Compound A-1 | 0.8 parts by mass |
| Isocyanate (Coronate (registered trademark) 2507 manufactured by Tosoh Corporation) | 15 parts by mass |
| Vinyl chloride-vinyl acetate copolymer (VMCH manufactured by Union Carbide Corporation) | 8 parts by mass |
| 2-butanone | 62 parts by mass |
| Cyclohexanone | 5 parts by mass |

The above components were subjected to a dispersion treatment with a sand mill to prepare a coating solution for forming the undercoat layer. The coating solution was dip-coated on the aforementioned conductive support and heat-treated at 140° C. for one hour to form an undercoat layer having a thickness of 6.1 μm.

(3) Forming Charge Generation Layer

| | |
|---|---|
| Y-type titanyl phthalocyanine (Y-TiOPc) | 20 parts by mass |
| Polyvinyl butyral resin (#6000-C manufactured by Denki Kagaku Kogyo Kabushiki Kaisha) | 10 parts by mass |

-continued

| | |
|---|---|
| t-butyl acetate | 900 parts by mass |
| MMP (4-methoxy-4-methyl-2-pentanone) | 100 parts by mass |

The above components were dispersed for 10 hours by using a sand mill as a dispersing machine to prepare a coating solution for forming the charge generation layer. The coating solution was dip-coated on the undercoat layer and was left at room temperature for one hour to form a charge generation layer having a thickness of 0.2 μm.

(4) Forming Charge Transport Layer

| | |
|---|---|
| Polycarbonate resin (FPC6550 manufactured by Mitsubishi Gas Chemical Company, Inc.) | 100 parts by mass |
| CTM-1 | 60 parts by mass |
| Dibutylhydroxytoluene (BHT) | 6 parts by mass |
| Tetrahydrofuran | 808 parts by mass |
| Toluene | 197 parts by mass |
| Dimethyl silicone oil (KF-96 manufactured by Shin-Etsu Chemical Co., Ltd.) | 0.12 parts by mass |

The above components were mixed to prepare a coating solution for forming the charge transport layer. The coating solution was dip-coated on the charge generation layer and heat-treated at 125° C. for 1.5 hours to form a charge transport layer having a thickness of 28 μm. A photoconductor 1 was prepared in this way.

Example 2

In Example 1, a photoconductor 2 was prepared in the same manner as in Example 1 except that the compound A-2 was used instead of the compound A-1 to prepare a coating solution for forming an undercoat layer. In the photoconductor 2, the thickness of the undercoat layer was 6.9 μm.

Example 3

In Example 1, a photoconductor 3 was prepared in the same manner as in Example 1 except that the compound A-3 was used instead of the compound A-1 to prepare a coating solution for forming an undercoat layer. In the photoconductor 3, the thickness of the undercoat layer was 7.0 μm.

Example 4

In Example 1, a photoconductor 4 was prepared in the same manner as in Example 1 except that CTM-2 was used instead of CTM-1 to prepare a coating solution for forming a charge transport layer. In the photoconductor 4, the thickness of the undercoat layer was 6.2 μm.

Example 5

In Example 1, a photoconductor 5 was prepared in the same manner as in Example 1 except that CTM-3 was used instead of CTM-1 to prepare a coating solution for forming a charge transport layer. In the photoconductor 5, the thickness of the undercoat layer was 6.6 μm.

Example 6

In Example 1, a photoconductor 6 was prepared in the same manner as in Example 1 except that CTM-4 was used instead of CTM-1 to prepare a coating solution for forming a charge transport layer. In the photoconductor 6, the thickness of the undercoat layer was 6.2 μm.

Example 7

In Example 1, a photoconductor 7 was prepared in the same manner as in Example 1 except that metal oxide particles 2 were used instead of metal oxide particles 1 to prepare a coating solution for forming an undercoat layer. In the photoconductor 7, the thickness of the undercoat layer was 6.3 μm.

Example 8

In Example 1, a photoconductor 8 was prepared in the same manner as in Example 1 except that metal oxide particles 3 were used instead of metal oxide particles 1 to prepare a coating solution for forming an undercoat layer. In the photoconductor 8, the thickness of the undercoat layer was 10.0 μm.

Example 9

In Example 1, a photoconductor 9 was prepared in the same manner as in Example 1 except that metal oxide particles 4 were used instead of metal oxide particles 1 to prepare a coating solution for forming an undercoat layer. In the photoconductor 9, the thickness of the undercoat layer was 5.9 μm.

Example 10

In Example 1, a photoconductor 10 was prepared in the same manner as in Example 1 except that type B titanyl phthalocyanine (B-TiOPc) was used instead of Y-TiOPc to prepare a coating solution for forming a charge generation layer. In the photoconductor 10, the thickness of the undercoat layer was 6.5 μm.

Example 11

In Example 1, a photoconductor 11 was prepared in the same manner as in Example 1 except that the dip-coating speed was changed so that the undercoat layer was formed to be thinner. In the photoconductor 11, the thickness of the undercoat layer was 1.5 μm.

Example 12

In Example 1, a photoconductor 12 was prepared in the same manner as in Example 1 except that the dip-coating speed was changed so that the undercoat layer was formed to be thicker. In the photoconductor 12, the thickness of the undercoat layer was 22 μm.

Comparative Example 1

In Example 1, a comparative photoconductor 1 was prepared in the same manner as in Example 1 except that a coating solution for forming an undercoat layer was prepared without adding the compound A-1. In the comparative photoconductor 1, the thickness of the undercoat layer was 8.0 μm.

Comparative Example 2

In Example 1, a coating solution for forming an undercoat layer was prepared without adding the compound A-1, a coating solution for forming a charge generation layer was prepared by using hydroxygallium phthalocyanine (OHGaPc) instead of Y-TiOPc, and a coating solution for forming a charge transport layer was prepared by using CTM-4 instead of CTM-1. With these coating solutions, a comparative photoconductor 2 was prepared in the same manner as in Example 1. In the comparative photoconductor 2, the thickness of the undercoat layer was 6.4 μm.

Comparative Example 3

In Example 1, a comparative photoconductor 3 was prepared in the same manner as in Example 1 except that the compound A'-1 was used instead of the compound A-1 to prepare a coating solution for forming an undercoat layer. In the comparative photoconductor 3, the thickness of the undercoat layer was 6.4 μm.

Comparative Example 4

In Example 1, a comparative photoconductor 4 was prepared in the same manner as in Example 1 except that the compound A'-2 was used instead of the compound A-1 to prepare a coating solution for forming an undercoat layer. In the comparative photoconductor 4, the thickness of the undercoat layer was 6.4 μm.

Comparative Example 5

In Example 1, a comparative photoconductor 5 was prepared in the same manner as in Example 1 except that the compound A'-3 was used instead of the compound A-1 to prepare a coating solution for forming an undercoat layer. In the comparative photoconductor 5, the thickness of the undercoat layer was 6.4 μm.

Comparative Example 6

In Example 1, a comparative photoconductor 6 was prepared in the same manner as in Example 1 except that the compound A'-4 was used instead of the compound A-1 to prepare a coating solution for forming an undercoat layer. In the comparative photoconductor 6, the thickness of the undercoat layer was 6.4 μm.

Comparative Example 7

In Example 1, a comparative photoconductor 7 was prepared in the same manner as in Example 1 except that a coating solution for forming an undercoat layer was prepared with neither metal oxide particles 1 nor the compound A-1 added. In the comparative photoconductor 7, the thickness of the undercoat layer was 6.3 μm.

Comparative Example 8

45 parts by mass of polyvinyl butyral (BL-S manufactured by Sekisui Chemical Co., Ltd.) was mixed with and dissolved in 450 parts by mass of 2-butanone, and the following components were mixed with the resultant product.

| | |
|---|---:|
| Metal oxide particles 5 | 450 parts by mass |
| Acrylic polyol (ACRYDIC (registered trademark) A814 manufactured by DIC Corporation, solid content 50%) | 50 parts by mass |

| | |
|---|---|
| Isocyanate (Coronate (registered trademark) 2507 manufactured by Tosoh Corporation, solid content 80%) | 100 parts by mass |
| 2-propanol | 55 parts by mass |

The mixture was then placed in a sand mill together with zirconia beads (average particle size: 0.5 mm) and dispersed for 10 hours to prepare a dispersion liquid. To the dispersion liquid, 0.002 parts by mass of dioctyl laurate was added to prepare a coating solution for forming an undercoat layer. The coating solution for forming the undercoat layer was dip-coated on the conductive support, and heat-treated at 160° C. for one hour to form an undercoat layer having a thickness of 6.2 μm. Next, a charge generation layer was formed on the undercoat layer in the same manner as in Example 1. Next, a coating solution for forming a charge transport layer was prepared in the same manner as in Example 1 except that a tributadiene derivative of the following structural formula (simply referred to as "tributadiene" in Table 1-1) was used instead of CTM-1. By using the coating solution for forming the charge transport layer, the charge transport layer was formed on the charge generation layer in the same manner as in Example 1. A comparative photoconductor 8 was prepared in this way.

[Chemical 24]

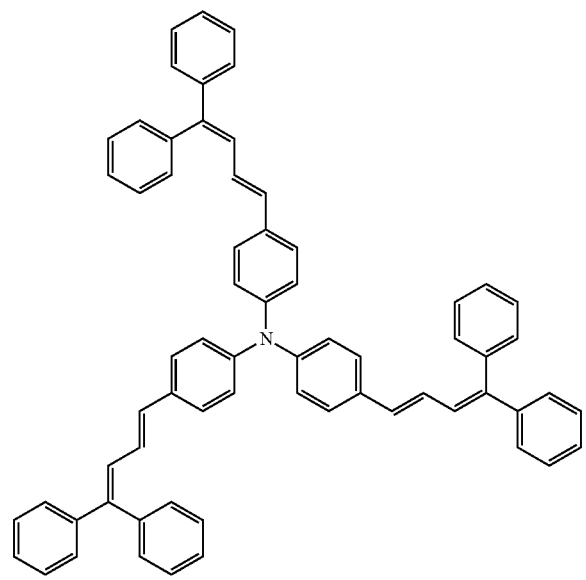

Example 13

The following components were stirred and dispersed in a sand mill for 24 hours to prepare a dispersion mother liquid.

| | |
|---|---|
| Polycarbonate resin (Z-400 manufactured by Mitsubishi Gas Chemical Company, Inc.) | 100 parts by mass |
| Tetrahydrofuran | 1,300 parts by mass |
| Toluene | 200 parts by mass |
| B-TiOPc | 1.8 parts by mass |

The following components were mixed with and dissolved in the dispersion mother liquor to prepare a coating solution for forming a photosensitive layer.

| | |
|---|---|
| CTM-2 | 66.7 parts by mass |
| Dibutylhydroxytoluene (BHT) | 6.7 parts by mass |
| Silicone oil (KF-96 manufactured by Shin-Etsu Chemical Co., Ltd.) | 0.15 parts by mass |

An undercoat layer having a thickness of 5.2 μm was formed on the conductive support in the same manner as in Example 1, and then the coating solution was dip-coated on the undercoat layer and heat-treated at 120° C. for one hour to form a photosensitive layer having a thickness of 25 μm. A photoconductor 13 was prepared in this way.

Example 14

In Example 13, a photoconductor 14 was prepared in the same manner as in Example 13 except that the coating solution for forming the photosensitive layer was prepared by further adding 33 parts by mass of the compound A-1. In the photoconductor 14, the thickness of the undercoat layer was 5.0 μm and the thickness of the photosensitive layer was 26 μm.

Comparative Example 9

In Example 13, a comparative photoconductor 9 was prepared in the same manner as in Example 13 except that the compound A'-1 was used instead of the compound A-1 to prepare a coating solution for forming an undercoat layer. In the comparative photoconductor 9, the thickness of the undercoat layer was 5.1 μm.

Comparative Example 10

In Example 14, a comparative photoconductor 10 was prepared in the same manner as in Example 14 except that the compound A'-1 was used instead of the compound A-1 to prepare a coating solution for forming an undercoat layer. In the comparative photoconductor 10, the thickness of the undercoat layer was 5.2 μm.

<Performance Evaluation of Photoconductor>

Bizhub PRESS (registered trademark) C1070 (manufactured by Konica Minolta, Inc.) was modified such that the charging application polarity, the development bias polarity, and the transfer application polarity can be switched between negative and positive by using an external power source. Furthermore, the modification was made in such a way that individual developing devices having their corresponding charging polarities were prepared so that images could be output in either of positively and negatively charged operations by replacing the developing devices. Regarding image exposure, the modification was made so that the amount of LD exposure could be adjusted to a greater extent. In this way, the modification was made so that images could be output regardless of whether the photoconductor was of a negatively charged operation type or a positively charged operation type. In addition, a surface potential meter was attached to measure the charge potential (Vo) and the post-exposure potential (Vi). Image memory (ghost) and potential stability during repeated use were evaluated with each of the photoconductors 1 to 14 and the comparative photoconductors 1 to 10 installed in the modified machine.

Figure 1B:
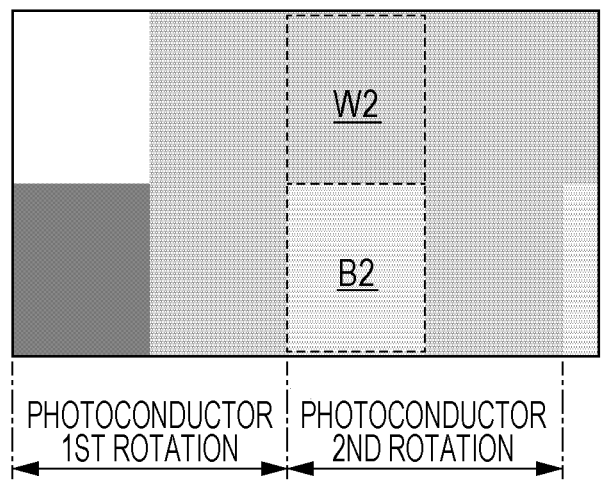
Figure 1C:
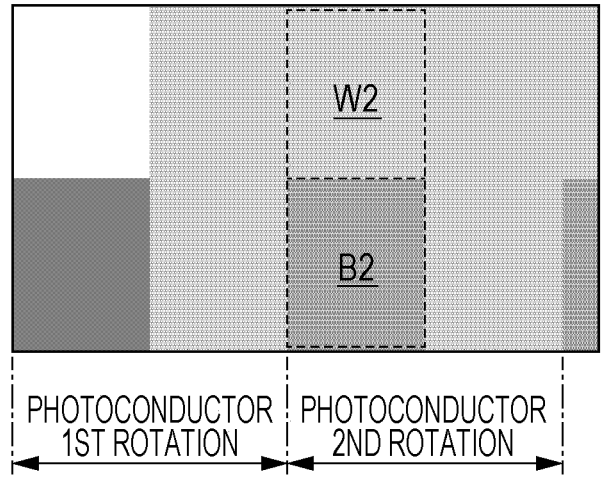

[Image Memory (Ghost)]
(1) Initial Memory
Under the environment of a temperature of 23° C. and a relative humidity of 50% RH, a print was made on a transfer material: "A3/POD gloss coat (A3 size, 100 g/m2)" (manufactured by Oji Paper Co., Ltd.) such that the transfer material had a solid black portion and a solid white portion during the first half of the first rotation of the photoconductor and a halftone portion during the second half of the first rotation of the photoconductor. Next, a print was made such that the transfer material had a halftone portion during the whole second rotation of the photoconductor. Next, concerning the second rotation, the image densities of the portions corresponding to the solid black portion in the first rotation (B2 in FIGS. 1A to 1C) and to the solid white portion in the first rotation (W2 in FIGS. 1A to 1C) were measured by using the Macbeth reflection densitometer "RD-918" (manufactured by Macbeth Inc.). Then, the difference ΔD=|B2−W2| between these image densities was calculated and evaluated according to the following criteria.

(Criteria)
⊙: ΔD is less than 0.01 (very good).
○: ΔD is 0.01 or more and less than 0.02 (good).
Δ: ΔD is 0.02 or more and less than 0.03 (problematic to some degree in practice).
x: ΔD is 0.03 or more (problematic in practice).

(2) Memory after Endurance
The evaluation of (1) above was followed by an endurance test in which a character image having an image ratio of 5% was continuously printed on both sides of 10,000 sheets in A4 landscape mode. After that, the evaluation of (1) was performed again to calculate the difference ΔD, which was evaluated in accordance with the above criteria.

[Potential Stability During Repeated Use]
The charge potential (Vo) and the post-exposure potential (Vi) were measured before and after the endurance test of (2) above. As the absolute value of a potential variation (ΔVo, ΔVi) between pre-endurance test and post-endurance test is smaller, the potential stability is better.

TABLE 1-1

Laminated type photoconductor

| | Undercoat layer | | | Charge generation layer | Charge transport layer | Image memory (ghost) | | Potential stability | |
|---|---|---|---|---|---|---|---|---|---|
| | Metal oxide particles | Electron transport material | Thickness [μm] | Charge generation material | Charge transport material | Initial | After endurance | Δ Vo (V) | Δ Vi (V) |
| Example 1 | Titanium oxide | A-1 | 6.1 | Y-TiOPc | CTM-1 | ⊙ | ○ | −9 | +5 |
| Example 2 | Titanium oxide | A-2 | 6.9 | Y-TiOPc | CTM-1 | ⊙ | ○ | −10 | +5 |
| Example 3 | Titanium oxide | A-3 | 7.0 | Y-TiOPc | CTM-1 | ⊙ | ○ | −20 | +4 |
| Example 4 | Titanium oxide | A-1 | 6.2 | Y-TiOPc | CTM-2 | ⊙ | ○ | −7 | +10 |
| Example 5 | Titanium oxide | A-1 | 6.6 | Y-TiOPc | CTM-3 | ⊙ | ○ | −5 | +11 |
| Example 6 | Titanium oxide | A-1 | 6.2 | Y-TiOPc | CTM-4 | ⊙ | ○ | −6 | +8 |
| Example 7 | Zinc oxide | A-1 | 6.3 | Y-TiOPc | CTM-1 | ⊙ | ○ | −18 | 0 |
| Example 8 | Tin oxide | A-1 | 10 | Y-TiOPc | CTM-1 | ⊙ | ○ | −25 | −2 |
| Example 9 | Aluminum oxide | A-1 | 5.9 | Y-TiOPc | CTM-1 | ⊙ | ○ | −7 | +12 |
| Example 10 | Titanium oxide | A-1 | 6.5 | B-TiOPc | CTM-1 | ⊙ | ○ | −2 | +11 |
| Example 11 | Titanium oxide | A-1 | 1.5 | Y-TiOPc | CTM-1 | ○ | ○ | −30 | +3 |
| Example 12 | Titanium oxide | A-1 | 22 | Y-TiOPc | CTM-1 | ○ | ○ | −15 | +20 |
| Comparative Example 1 | Titanium oxide | — | 8.0 | Y-TiOPc | CTM-1 | ○ | Δ (negative) | +10 | +40 |
| Comparative Example 2 | Titanium oxide | — | 6.4 | OHGaPc | CTM-4 | Δ (negative) | X (negative) | +20 | +55 |
| Comparative Example 3 | Titanium oxide | A'-1 | 6.4 | Y-TiOPc | CTM-1 | Δ (negative) | X (negative) | −10 | +60 |
| Comparative Example 4 | Titanium oxide | A'-2 | 6.4 | Y-TiOPc | CTM-1 | Δ (negative) | X (negative) | +5 | +58 |
| Comparative Example 5 | Titanium oxide | A'-3 | 6.4 | Y-TiOPc | CTM-1 | Δ (negative) | X (negative) | +10 | +77 |
| Comparative Example 6 | Titanium oxide | A'-4 | 6.4 | Y-TiOPc | CTM-1 | Δ (negative) | X (negative) | +18 | +62 |
| Comparative Example 7 | None | — | 6.3 | Y-TiOPc | CTM-1 | Δ (negative) | X (negative) | +52 | +82 |
| Comparative Example 8 | Zinc oxide | Alizarin | 6.2 | Y-TiOPc | Tributadiene | Δ (positive) | X (positive) | −78 | −5 |

* (negative): negative memory,
* (positive): positive memory

TABLE 1-2

Single-layer type photoconductor

| | Undercoat layer | | | Photosensitive layer | | | Image memory (ghost) | | Potential stability | |
|---|---|---|---|---|---|---|---|---|---|---|
| | Metal oxide particles | Electron transport material | Thickness [μm] | Charge generation material | Charge transport material | Electron transport material | Initial | After endurance | Δ Vo (V) | Δ Vi (V) |
| Example 13 | Titanium oxide | A-1 | 5.2 | B-TiOPc | CTM-2 | — | ○ | ○ | −34 | +24 |

TABLE 1-2-continued

| | Undercoat layer | | | Photosensitive layer | | | Image memory (ghost) | | Potential stability | |
| --- | --- | --- | --- | --- | --- | --- | --- | --- | --- | --- |
| | Metal oxide particles | Electron transport material | Thickness [μm] | Charge generation material | Charge transport material | Electron transport material | Initial | After endurance | Δ Vo (V) | Δ Vi (V) |
| Example 14 | Titanium oxide | A-1 | 5 | B-TiOPc | CTM-2 | A-1 | ○ | ○ | −33 | +20 |
| Comparative Example 9 | Titanium oxide | A'-1 | 5.1 | B-TiOPc | CTM-2 | — | Δ (negative) | X (negative) | −10 | +72 |
| Comparative Example 10 | Titanium oxide | A'-1 | 5.2 | B-TiOPc | CTM-2 | A'-1 | Δ (negative) | X (negative) | −25 | +62 |

*(negative): negative memory

Table 1-1 above shows the results of the evaluation of laminated type photoconductors. As compared with the photoconductors of Comparative Examples 1 to 8, the photoconductors of Examples 1 to 12 suppressed the occurrence of image memory (ghost) at the beginning and after printing on 10,000 sheets. In addition, the photoconductors of Examples 1 to 12 had a small post-exposure potential variation (ΔVi) between before and after printing on 10,000 sheets as compared with the photoconductors of Comparative Examples 1 to 7, and a small charge potential variation (ΔVo) between before and after printing on 10,000 sheets as compared with the photoconductor of Comparative Example 8.

Table 1-2 above shows the results of the evaluation of single-layer type photoconductors. As compared with the photoconductors of Comparative Examples 9 and 10, the photoconductors of Examples 13 and 14 suppressed the occurrence of image memory (ghost) at the beginning and after printing on 10,000 sheets. In addition, the photoconductors of Examples 13 and 14 had a small post-exposure potential variation (ΔVi) between before and after printing on 10,000 sheets as compared with the photoconductors of Comparative Examples 9 and 10.

From the above results, it has been found that the photoconductor according to the present invention is capable of suppressing the occurrence of image memory (ghost) and is excellent in potential stability during long-term repeated use.

Although embodiments of the present invention have been described and illustrated in detail, the disclosed embodiments are made for purposes of illustration and example only and not limitation. The scope of the present invention should be interpreted by terms of the appended claims.

What is claimed is:

1. An electrophotographic photoconductor in which at least an undercoat layer and a photosensitive layer are laminated in an order mentioned on a conductive support, wherein both the undercoat layer and the photosensitive layer contain a compound represented by a formula A below:

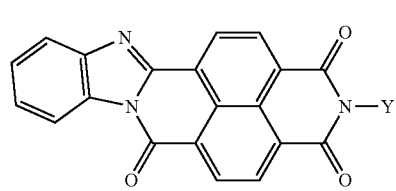

(FORMULA A)

wherein Y in the above formula A is a group represented by:

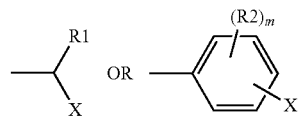

wherein R1 and R2 are each independently an alkyl group having 1 to 6 carbon atoms, m is an integer of 1 to 4, and X is each independently a group selected from a group 1 below:

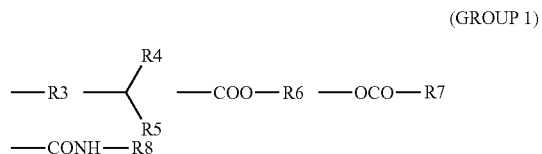

(GROUP 1)

wherein R3 to R8 in the above group 1 are each independently an alkyl group having 1 to 6 carbon atoms.

2. The electrophotographic photoconductor according to claim 1, wherein R3 to R5 in the group 1 are each independently a methyl group or an ethyl group.

3. The electrophotographic photoconductor according to claim 1, wherein R6 to R8 in the group 1 are each independently an alkyl group having 3 to 5 carbon atoms.

4. The electrophotographic photoconductor according to claim 1, wherein the undercoat layer further contains metal oxide particles.

5. The electrophotographic photoconductor according to claim 4, wherein the metal oxide is at least one selected from the group consisting of titanium oxide, zinc oxide, tin oxide, and aluminum oxide.

6. The electrophotographic photoconductor according to claim 1, wherein
the photosensitive layer includes a charge generation layer and a charge transport layer, and
at least the undercoat layer, the charge generation layer, and the charge transport layer are laminated in the order mentioned on the conductive support.

7. The electrophotographic photoconductor according to claim 6, wherein the charge generation layer contains a titanyl phthalocyanine compound.

8. The electrophotographic photoconductor according to claim 6, wherein the charge transport layer contains at least one selected from the group consisting of compounds represented by the formulas 1 to 4 below:

(FORMULA 1)

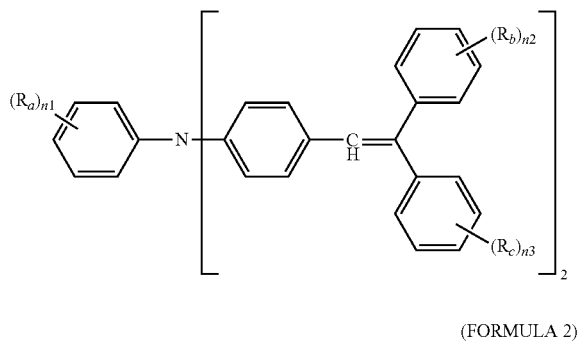

(FORMULA 2)

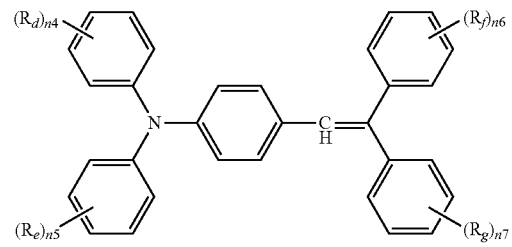

(FORMULA 3)

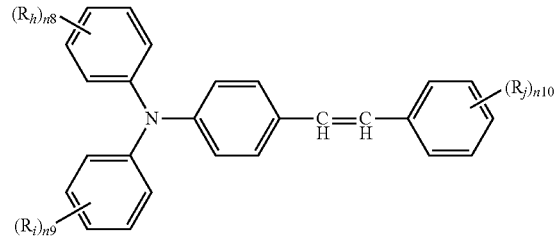

(FORMULA 4)

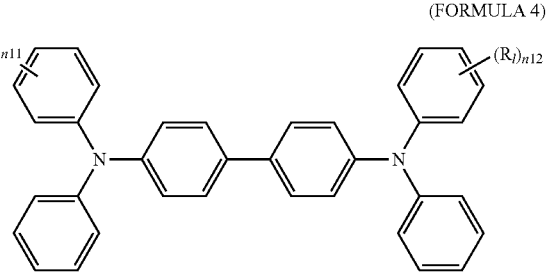

wherein, in the formulas 1 to 4,
$R_a$ to $R_l$ are each independently an alkyl group having 1 to 3 carbon atoms, an alkoxy group having 1 to 3 carbon group, or a halogen atom, and
n1 to n12 are each independently an integer of 0 to 5.

9. The electrophotographic photoconductor according to claim 1, wherein the undercoat layer has a thickness of 5 to 20 μm.

* * * * *